United States Patent [19]
Hughes et al.

[11] Patent Number: 5,962,284
[45] Date of Patent: Oct. 5, 1999

[54] ACRYLAMIDASE ENZYMES

[75] Inventors: Jonathan Hughes; Yvonne Christine Armitage, both of Huddersfield, United Kingdom

[73] Assignee: Ciba Specialty Chemicals Water Treatments Limited, Bradford, United Kingdom

[21] Appl. No.: 09/130,644

[22] Filed: Aug. 7, 1998

[30] Foreign Application Priority Data

Aug. 7, 1997 [GB] United Kingdom ............... 9716764

[51] Int. Cl.⁶ .................. C12P 13/02; C12N 9/80; C07C 1/02; C08J 33/00
[52] U.S. Cl. .................. 435/129; 435/228; 435/262; 524/827
[58] Field of Search .................... 435/228, 129, 435/252.1, 262; 524/827

[56] References Cited

U.S. PATENT DOCUMENTS

| | | |
|---|---|---|
| 4,687,807 | 8/1987 | Wetegrove et al. ............ 524/827 |
| 4,742,114 | 5/1988 | Wetegrove et al. ............ 524/827 |
| 4,786,679 | 11/1988 | Wetegrove et al. ............ 524/827 |

FOREIGN PATENT DOCUMENTS

| | | |
|---|---|---|
| 0 272 025 | 6/1988 | European Pat. Off. . |
| 0 272 026 | 6/1988 | European Pat. Off. . |
| 0 329 324 | 8/1989 | European Pat. Off. . |
| 0 329 325 | 8/1989 | European Pat. Off. . |
| 0 393 916 | 10/1990 | European Pat. Off. . |
| 97/29136 | 8/1997 | WIPO . |

OTHER PUBLICATIONS

Brennan et al. Amidase active whole cells of Corynebacterium nitilophilus for ammonium acrylate production. Biotechnology Letters 17(5):513–518, May 1995.

*Primary Examiner*—Eggerton A. Campbell
*Assistant Examiner*—Devesh Srivastava
*Attorney, Agent, or Firm*—David R. Crichton

[57] ABSTRACT

Acrylamidase enzymes are provided which have acrylamidase activity at pH 4.0 which is at least 50% of their acrylamidase activity at pH 7.0. Such enzymes can be produced by the novel microorganisms Rhodococcus strains NCIMB 40889 and NCIMB 40755. Such enzymes and microorganisms can be used for reducing free acrylamide in polyacrylamides which are produced at low pH and in particular cationic and substantially non-ionic polyacrylamides.

5 Claims, No Drawings

ACRYLAMIDASE ENZYMES

The present invention relates to new acrylamidase enzymes, microorganisms which can produce such enzymes and the use of the enzymes and microorganisms.

It is well known to convert acrylamide to acrylic acid (or salt thereof, for instance ammonium acrylate) using amidase enzymes. Amidase enzymes which show this activity are referred to herein as acrylamidase enzymes.

In particular it is taught in EP-A-329325 to treat acrylamide polymers with acrylamidase enzymes so as to reduce the free acrylamide content of the polymer. EP-A-329325 describes treatment of acrylamide polymer gel with an amidase enzyme so as to reduce the free acrylamide content. Our International Application WO97/29136 (not published before the priority date of the present application) describes processes in which polyacrylamide gel is produced and the levels of acrylamidie monomer reduced to very low levels and/or reduced during the standard production process without the need for separate and extensive treatment stages.

Particular problems arise with the treatment of polyacrylamides which have been formed at low pH (eg pH 5 or below). This is often done for instance to control the polymerisation reaction. Certain polymerisation initiators are most effective at low pH, so the monomer solution is buffered to low pH during the polymerisation reaction.

This applies in particular to cationic polyacrylamides (ie polymers formed from a monomer blend comprising acrylamide and one or more cationic monomers) and substantially non-ionic polyacrylamides (ie acrylamide homopolymers and polymers formed from a monomer blend comprising acrylamide, one or more other non-ionic monomers and substantially no ionic monomer). Some anionic polyacrylamides (ie polymers formed from acrylamide and one or more anionic monomers) can also be formed at pH below 6, although this is not so common dS for cationic and non-ionic acrylamides. In such cases, the polyacrylamides are generally produced at low pH in order to optimise the effectiveness of the initiator systems which are used. The buffer system which maintains the low pH (about pH 4) normally includes an organic acid such as adipic acid. This acid also stabilises cationic monomers (where present) against hydrolysis, which can be a problem when the product polymer is added to hard water for use, and is thus present in larger amounts when cationic polyacrylamides are produced than when, say, non-ionic polyacrylamides are produced.

Therefore some polyacrylamides, in particular cationic and non-ionic polyacrylamides, are often formed at a low pH of around pH 4.

It is generally accepted, however, that acrylamidase enzymes have peak activity and effectiveness at neutral pH (around pH 6 or 7). It is generally accepted that, as pH decreases and the relevant medium becomes more acidic, acrylamidase enzymes become less effective at converting acrylamide to acrylic acid or salt thereof. Many acrylamidase enzymes which give good performance at pH 6 or 7 give very poor performance at pH 3 or 4.

Therefore it is standard practice to adjust the pH of a polyacrylamide which has been formed at low pH from around pH 4 to around pH 6 or 7 before treating it with acrylamidase to reduce free acrylamide content. EP-A-393,916, for instance, explains that it is standard to adjust the pH of cationic polyacrylamides before treatment with acrylamidase. U.S. Pat. No. 4,786,679 and U.S. Pat. No. 4,742,114 describe treatment of unspecified "polymer latex" and "polyacrylamide latex" at pH of 8.35 and 7.

In EP-A-272026, acrylamidase enzymes are described for treating a polymer latex (i.e. a polymer emulsion) of various polyacrylamides. Treatment of anionic, non-ionic and cationic polyacrylamides is described. However, each polymer latex is pH adjusted to about 6 before it is treated with the acrylamidase. Having to use such a system is inconvenient, as it requires an additional treatment step between producing and treating a cationic polyacrylamide. If such a treatment were to be included in an industrial scale process, it would be necessary either to introduce additional treatment stages in the process, and consequently to increase the time and inconvenience involved, or to provide additional equipment which enables treatment to be carried out within the timescale of the process.

The related publication EP-A-272,025 additionally describes treatment of a cationic latex at both pH 4 and pH 6. Although treatment at pH 6 is effective in reducing free acrylamide levels, the results given demonstrate that treatment with the acrylamidase used in that example is ineffective at pH 4. Reduction of free acrylamide is not achieved.

U.S. Pat. No. 4,687,807 explains that optimum amidase activity is obtained at pH between 6 and 7. It also describes treatment of cationic polyacrylamides at acidic pH. In this reference, the cationic polyacrylamides are produced in the form of a polymer emulsion and the pH of the emulsion is then adjusted. In two of the examples the pH is adjusted to pH 3.8 and pH 5.5. The pH-adjusted latex is then treated with an amidase so as to reduce free acrylamide levels. The examples show that treatment is not particularly effective. At pH 5.5, 24 hours are required to reduce the acrylamide monomer level from 9 ppm to 200 ppm, and after a further 24 hours acrylamide monomer content is reduced only to 150 ppm. Treatment at pH 3.8 shows that the performance of the amidase enzyme has decreased significantly. After 24 hours monomer content is reduced from 900 to 400 ppm, and after another 24 hours, it is reduced only to 380 ppm. We have calculated that the activity at pH 5.5 is approximately 33% of the equivalent activity at pH 7 and the activity at pH 3.8 is approximately 23% of the equivalent activity at pH 7. In this document Example 10 describes a polymer which contains a small amount of cationic monomer, although it contains a much larger amount (40%) of anionic monomer and would not be classed as a cationic polyacrylamide. The example describes treatment of the polymer with an amidase enzyme and without pH adjustment but results appear to be predicted rather than achieved.

It would be desirable to be able to treat cationic polyacrylamides and other polyacrylamides which are produced at low pH (especially non-ionic polyacrylamides) so as to reduce their free acrylamide content without having to subject them to pH adjustment before treatment. It would also be desirable to find a more effective method of reducing the acrylamide monomer content in such polyacrylamides.

According to the invention we provide an acrylamidase enzyme which has an acrylamidase activity at pH 4.0 which is at least 50% of its acrylamidase activity measured at pH 7.0.

We have surprisingly found that it is possible to provide an acrylamidase enzyme which, contrary to generally accepted properties of acrylamidase enzymes, can act effectively at pH 4.0. Such an enzyme can be used for treating polyacrylamides produced at about pH 4.0 directly, without an intervening pH treatment stage.

The provision of such enzymes has however revealed a further problem. As explained above, a commonly used buffer acid for the production of polyacrylamides is adipic acid, which is present in significant amounts in the production of cationic polyacrylamides. We have found that some acrylamidases, although they are active at pH 4.0 under most circumstances, are inhibited in the presence of adipic acid. Such enzymes are therefore effective only if the polyacrylamide has been produced using a different buffer acid.

We have also surprisingly found that it is possible to provide acrylamidase enzymes which are active at low pH in the presence of adipic acid. Specifically, in a preferred aspect of the invention we provide an acrylamidase enzyme of the invention which additionally has an acrylamidase activity at pH about 4 in the presence of about 15 mM adipic acid which is at least about 30% of its acrylamidase activity measured at pH about 4 in the absence of adipic acid. Preferred enzymes are also active at low pH in the presence of succinic acid, is they have an acrylamidase activity at pH about 4 in the presence of about 15 mM succinic acid which is at least about 30% of its acrylamidase activity measured at pH about 4 in the absence of succinic acid.

The acrylamidase enzymes of this aspect of the invention are especially useful for treatment of cationic polyacrylamides, because they are active in the presence of the standard buffer.

Preferred enzymes of the invention have both the property of retaining at least 50% of their acrylamidase activity at pH 4 and retaining at least 30% of their acrylamidase activity in the presence of 15 mM adipic acid.

In this specification acrylamidase activity can be measured by any suitable method, for instance measuring specific acrylamidase activity of an enzyme or microorganism, or by testing the ability of an enzyme or microorganism to reduce residual acrylamidase monomer in a polymer. Any test which can validly be carried out and compared at pH 7 and 4 may be used. A preferred test method is as follows:

The amidase activity is measured by the addition of an amidase active cell suspension under the following standard conditions: in pH 7 (50 mM sodium phosphate buffer) or pH 4 (60 mM citric acid/77 mM disodium hydrogen phosphate buffer) or pH 5 (48 mM citric acid/103 mM disodium hydrogen phosphate buffer), 50 mM (3554 ppm) acrylamide at 30° C. For measurement of Km (see below) the same conditions can be used, except that the acrylamide concentration is of course varied. One unit (U) of amidase activity hydrolyses 1 micromole of acrylamido per minute under the above conditions. The specific activity is the amount of units of activity present per dry gram of cell material. The relative activity is the % activity relative to activity at ph 7.

In this specification, comparison of acrylamidase activity in the presence of adipic acid and in the absence of adipic acid is measured by the following adipic acid activity assay:

To an assay mixture at pH 4 as described for measurement of activity at pH 4 and pH 7 is added adipic acid to give the concentrations required. Cell suspension is then added to the assay mixture. The amidase activity of each suspension is then measured. The relative activity is % activity relative to activity in the absence of adipic acid.

In the invention the acrylamidaze enzyme shows activity at pH 4.0 which is at least 50% of its acrylamidase activity at pH 7.0. Preferably it retains at pH 4.0 at least 60%, preferably at least 70%, and even at least 90%, of its pH 7.0 activity. For some enzymes activity at pH 4.0 may even be greater than at pH 7.0.

Preferred enzymes according to the invention also retain their activity in the presence of adipic acid. This is tested by comparing acrylamidase activity in the presence of 15 mM adipic acid with acrylamidase activity in the absence of adipic acid. Preferably activity in the presence of 15 mM adipic acid is at least 30%, more preferably at least 35%, of activity in the absence of adipic acid. Preferred enzymes also retain their activity in the presence of higher concentrations of adipic acid. For instance, activity in the presence of 25 mM adipic acid is preferably at least 25% of that in the absence of adipic acid. Activity in the presence of 50 mM adipic acid is preferably at least 10% of that in the absence of adipic acid.

Preferably the enzyme shows the same properties when succinic acid is used instead of adipic acid.

Preferred amidase enzymes have adequate or good acrylamidase activity at pH 7. Such enzymes are useful for treating polyacrylamides which are produced at about pH 7, for instance some anionic polyacrylamides, as well as polyacrylamides produced at about pH 4 using the conditions above for acrylamidase activity.

Particularly preferred acrylamidases of the invention have a low Km for acrylamide. One preferred application of the amidases of the invention is treatment of polyacrylaiides so as to reduce residual acrylamide level. If the enzyme has a very low Km, this means it has very good scavenging ability and can thus provide a polyacrylamide having very low, sometimes undetectable, levels of acrylamide monomer. Preferably Km is below 20 mM, more preferably below 15 mM or 10 mM and may even be below 5 mM. In this specification, Km is Km for acrylamide measured at pH 4.0.

Particularly preferred amidases of the invention can be produced by culturing specific microorganisms. One of these is a Rhodococcus species deposited (as Rhodococcus species) at the National Collections of Industrial and Marine Bacteria (NCIMB), 23 St Machar Drive, Aberdeen AB2 1RY, Scotland, UK under the provisions of the Budapest Treaty on Jul. 14, 1995 (by Jonathan Hughes of Allied Colloids Ltd, P O Box 38, Low Moor, Bradford, West Yorkshire BD12 0JZ, England, and on behalf of Allied Colloids Ltd.) and having Deposit Number NCIMB 40755. We believe the isolate is of species *Rhodococcus erythropolis.*

This Rhodococcus isolate has the following properties

| Decomposition of: | |
|---|---|
| Adenine | + |
| Tyrosine | + |
| Urea | + |
| Growth on sole carbon source: | |
| Inositol$^1$ | + |
| Maltose$^1$ | − |
| Mannitol$^1$ | + |
| Rhamnose$^1$ | − |
| Sorbitol$^1$ | + |
| m-hydroxybenzoic acid$^2$ | − |
| Sodium adipate$^2$ | + |
| Sodium benzoate$^2$ | − |
| Sodium citrate$^2$ | + |
| Sodium lactate$^2$ | + |
| Sodium glutamate$^2$ | + |
| L-tyrosine$^2$ | + |
| Glycerol$^1$ | + |
| Trehalose | + |
| p-hydroxybenzoic acid$^2$ | + |
| D-mannose$^1$ | + |
| Acetamide$^2$ | + |
| D-galactose$^1$ | − |
| Enzymatic test:* | |
| α-glucosidase | + |
| Cysteine arylamidase | − |
| Valine arylamidase | + |

-continued

| Growth in the presence of: | |
|---|---|
| 5% NaCl | + |
| Sodium azide[3] | + |

[1]1% w/v
[2]0.1% w/v
[3]0.02% w/v
*Bioconnections/Rosco Diagnostics

This microorganism produces an amidase which has activity at pH 4.0 which is about 65% of its activity at pH 7.0. Under the preferred test protocol given above it gives the following results:
Rhodococcus NCIMB 40755

| pH | Specific Activity (U/g) | Relative Activity (%) |
|---|---|---|
| 4 | 2,506 | 65 |
| 5 | 2,835 | 73 |
| 7 | 3,860 | 100 |

This enzyme is particularly useful for treating at pH 4 cationic polyacrylamides which have not been made in the presence of adipic acid buffer, since it does not perform well in the presence of adipic acid. Other suitable buffers for cationic polyacrylamide production include acetic acid, glutaric acid and citric acid, and mixtures thereof.

This microorganism produces an acrylamidase which shows Km for acrylamide of 6 mM at pH 4.0.

A particularly preferred acrylamidase enzyme is produced by the *Rhodococcus erythropolis* microorganism deposited (as *Rhodococcus erythropolis*) at NCIMB (see above for full name and address) under the provisions of the Budapest Treaty on Aug. 5, 1997, also by Dr Jonathan Hughes on behalf of Allied Colloids Ltd (see above), and having the accession number NCIMB 40889.

This Rhodococcus isolate has the following properties. Mycolic acids are present. The cell wall diamino acid is meso-DAP. The fatty acids present are straight chain saturated and unsaturated fatty acids together with branched chain acid having the methyl group on carbon 10; in particular 10 methyloctadecanoic acid (tuberculostearic acid).

| Decomposition of: | |
|---|---|
| Adenine | + |
| Tyrosine | + |
| Urea | + |
| Growth on sole action sources: | |
| Inositol[1] | − |
| Maltose[1] | − |
| Mannitol[1] | + |
| Rhamnose[1] | − |
| Sorbitol[1] | + |
| m-hydroxybenzoic acid[2] | − |
| Sodium adipate[2] | + |
| Sodium benzoate[2] | − |
| Sodium citrate[2] | + |
| Sodium lactate[2] | + |
| Sodium glutamate[2] | (+) 11 days |
| L-tyrosine[2] | − |
| Glycerol[1] | + |
| Trehalose[1] | + |
| p-hydroxybenzoic acid[2] | − |
| D-mannose[1] | − |
| Acetamide[2] | + |
| D-galactose | − |

-continued

| Enzymatic tests: | |
|---|---|
| α-glucosidase | + |
| Cysteine acrylamide | + |
| Valine arylamide | ND |
| Growth in the presence of: | |
| 5% NaCl | + |
| Sodium azide[3] | − |

[1]1% w/v
[2]0.1% w/v
[3]0.2% w/v
ND = Not determined.

This microorganism produces an acrylamidase enzyme which rotains at pH 4 about 91% of its acrylamidase activity at pH 7. Under the preferred test protocol given above it gives the following results:
Rhodococcus MCIMB 40889:

| pH | Specific Activity (U/g) | Relative Activity (%) |
|---|---|---|
| 4 | 3,789 | 91.3 |
| 7 | 4,146 | 100 |

It is additionally especially advantageous because it retains significant activity in the presence of adipic acid, and succinic acid. Under the preferred test protocol given above it gives the following results:

| Adipic Acid (mM) | Specific Activity (U/g) | Relative Activity (%) |
|---|---|---|
| 0 | 4,936 | 100 |
| 5 | 4,705 | 95 |
| 10 | 3,421 | 69 |
| 15 | 1,891 | 38 |
| 22.5 | 1,486 | 30 |
| 25 | 1,442 | 29 |
| 50 | 609 | 12 |

This microorganism produces an acrylamidase enzyme which shows Km for acrylamide of 11.6 mM at pH 4.0.

According to a second aspect of the invention we provide an acrylamidase enzyme which can be produced by culturing Rhodococcus strain NCIMB 40889 or Rhodococcus strain NCIMB 40755 or a mutant of either having the ability to produce an acrylamidase.

According to a third aspect of the invention we provide a microorganism which is Rhodococcus strain NCIMB 40889 or Rhodococcus strain NCIMB 40755 or a mutant of either having the ability to produce an acrylamidase.

According to a fourth aspect of the invention we provide a microorganism whose cells or cell material show acrylamidase activity at about pH 4 which is at least about 50% of their acrylamidase activity at about ph 7. Such microorganisms include those which produce only one acrylamidase of the invention and those which produce more than one acrylamidase, one with significant activity at pH 7 and one with significant activity at pH 4. Any of the properties of the acrylamidase discussed above are also applicable in this aspect of the invention.

The acrylamidases and microorganisms of the invention are useful for conversion of acrylamide to acrylic acid in various environments. The acrylamidases and microorganisms may be used to produce acrylic acid monomer or salt thereof, especially ammonium acrylate, from acrylamide starting material. Preferably they are used kin a process of reducing the residual acrylamide content of a polyacrylamide by contacting the polyacrylamide with an acrylamidase of the invention or a microorganism of the invention. In the process any of the acrylamidases and microorganisms of the invention having any of the preferred features discussed above may be used.

All types of polyacrylamide, anionic, non-ionic and cationic, may be treated. The invention is particularly appropriate for treatment of polyacrylamides which have been produced at low pH, especially cationic and substantially non-ionic polyacrylamides.

Cationic polyacrylamides are normally copolymers or terpolymers of acrylamide with one or more cationic monomers. Cationic monomers are normally present in an amount of 3 to 90% by weight, often below 70% and preferably below 50%, by weight based on the total weight or monomers. Any of the conventional cationic monomers may be used such as diallyl ammonium monomers for instance DADMAC (diallyl dimethyl ammonium chloride) or cationic esters, for instance diallyl amino alkyl (meth) acrylates such as DMAEA (dimethyl aminoethyl acrylate) or DMAEMA (dimethyl aminoethyl methacrylate) often as acid addition or quaternary ammonium salts or cationic amides such as DMAPMA.

Cationic polyacrylamides can be made amphoteric by the inclusion of a minor amount (less than the amount of cationic monomer) of anionic monomer, usually in an amount of not more than 10 to 5 wt %.

Cationic polyacrylamides generally have intrinsic viscosity (IV) above 8 and usually above 10 or 12 dl/g, typically above 14 dl/g. Generally IV is not above 20 or 25 dl/g. In this specification intrinsic viscosity is measured by suspended level viscometer at 25° C. in 1M NaCl buffered to pH 7.

The polyacrylamide may be non-ionic, in which case it will be a homopolymer of acrylamide or a copolymer or terpolymer with other non-ionic monomers, such as methacrylamide. It may contain a minor amount (below 3 wt. % and usually below 2 or 1 wt. %) of ionic monomer. In particular it may contain minor amounts of hydrolysed acrylamide (acrylate or acrylic acid) monomer.

Anionic polyacrylamides are generally copolymers or terpolymers of acrylamide with one or more anionic monomers Anionic monomers are usually present in an amount of 3 to 90% by weight, often below 70% and preferably below 50%, by weight based on the total weight of monomer. Any of the typical anionic monomers may be used such as ethylenically unsaturated carboxylic or sulphonic monomers, especially acrylic acid (including water-soluble salts thereof).

The polyacrylamide, when anionic or non-ionic, preferably has such a high molecular weight that its intrinsic viscosity is at least 6 or 10 dl/g and frequently at least 15, 20 or even 30 dl/g. It is usually not above 50 dl/g.

Any of the above polymers can be provided in any suitable form, including gel, emulsion and dry dispersion form. Gel polymers are preferred. When the polymer is in the form of a dispersion in non-aqueous liquid which is dry (containing below 15 wt. %, preferably below 10 wt. % water based on weight of dispersion) the acrylamide may be added to the dispersion so as to be active, as described in EP-A-329,324, when dispersed into water for 2 hours at 25° C. Alternatively, some acrylamidases can effect reduction of acrylamide even at the low water contents in the dispersion itself. All of these polymer forms may be made in any conventional manner.

The process is particularly suitable when the polyacrylamide is made by any of the processes described in our International Patent Publication No. WO97/29136.

In particular it is suitable as a process for the production of substantially dry particles of a polyacrylamide comprising providing aqueous polyacrylamide gel particles contaminated with acrylamide monomer applying acrylamidase enzyme to the aqueous gel particles whilst they are at a temperature of from 50 to 95° C., and substantially immediately passing the aqueous gel particles to a drying stage and subjecting them in that stage to a temperature of at least 45° C. (preferably at least 50 or 60° C.) so as to produce substantially dry particles of polyacrylamide, in which the acrylamidase enzyme is an enzyme according to the invention.

The microorganism NCIMB 40889 and the acrylamidase it produces are particularly suitable for this process since they are believed to be active at a relatively high temperature and/or very fast acting.

The polyacrylamide is preferably cationic or non-ionic.

A further process in which the acrylamidase enzymes of the invention can be used is a process for the production of substantially dry particles of a polyacrylamide comprising providing aqueous polyacrylamide gel particles contaminated with acrylamide monomer applying acrylamidase enzyme having a Km for acrylamide not more than 10 mM to the aqueous gel particles whilst they are at a temperature of 50 to 95° C.

holding the aqueous gel particles to which acrylamidase has been applied in a holding stage at a temperature of from 20 to 70° C. for not more than 30 minutes, and then passing the particles to a drying stage and subjecting them in that stage to a temperature of at least 45° C. (preferably at least 50 or 60° C.) to produce substantially dry particles, the process being carried out such that the final content of acrylamide monomer in the substantially dry particles is below measurable levels, and the amidase enzyme being an enzyme according to the invention.

The polyacrylamide is preferably cationic or non-ionic.

A further process of the invention is a process for the production of substantially dry particles of a polyacrylamide comprising providing aqueous polyacrylamide gel particles contaminated with acrylamide monomer, applying acrylamidase enzyme which has a, Km for acrylamide of not more than 10 mM, preferably not more than 5 mM, to the aqueous gel particles whilst they are at a temperature of 50 to 95° C., holding the aqueous gel particles to which acrylamidase has been applied to a holding stage in the cold zone of a fluid bed drier at a temperature of from 20 to 70° C. for not more than 30 minutes, and then passing the particles to a drying stage in the hot zone of a fluid bed drier and subjecting them in that stage to a temperature of at least 45° C. (preferably at least 50 or 60° C.) so as to provide substantially dry particles of polyacrylamide, in which the amidase enzyme is an enzyme according to the invention.

The polyacrylamide is preferably cationic or non-ionic.

The microorganism NCIMB 40755 is particularly suitable for these latter two processes, because it shows low Km for acrylamide. When this microorganism or its acrylamidase are used the polyacrylamide (especially if cationic) is preferably produced in the presence of a buffer other than adipic acid, for instance acetic, succinic, glutaric or citric acid and mixtures thereof. Km in those processes is generally Km at pH 4.0.

In preferred processes of the invention polyacrylamide, preferably cationic or non-ionic polyacrylamide, is produced at an acidic pH (for instance pH 2 to 5, preferably pH 3 to 4.5) and is treated with an acrylamidase of the invention without adjustment of the pH.

In further preferred processes polyacrylamide, preferably cationic polyacrylamide, is produced in the presence of adipic acid buffer, preferably in an amount of from 0.5 to 10% by weight of total solids (ie monomer plus adipic acid), more preferably 0.5 to 5%, for instance 1 to 2 or 3%. The acrylamidase of the invention is contacted with the polyacrylamide in the presence of the adipic acid. The adipic acid may be used in combination with other buffers such as citric, glutaric or acetic acid. Alternatively, succinic acid may be used.

The process of the invention may also be applied to those processes as described in our earlier publication EP-A-329,325, in particular for treatment of cationic and non-ionic polymers.

The enzymes and microorganisms of the invention are particularly suitable for use in the process described in our copending international application number PCT/GB98/02362, filed Aug. 6, 1998 and claiming priority from GB 9716767.0.

The processes, microorganisms and acrylamidase enzymes of the invention can be used for the treatment of various polyacrylamides. The processes, microorganisms and enzymes of the invention may in particular be used for treatment of any polyacrylamide which is produced at a low pH, for instance from pH 2 to 5, preferably pH 3 to 4. For instance, any of the aspects of the invention are applicable to treatment of non-ionic polyacrylamides which have been produced at a pH of from 2 to 5, preferably 3 to 4, and cationic polyacrylamides which have been produced at pH of from 2 to 5, preferably from 3 to 4.5. Any of the preferred features of the invention discussed above are also applicable to treatment of anionic polyacrylamides, especially if produced at pH below 6, eg about pH 5. In particular the invention is useful in processes in which the polyacrylamide is produced at a defined pH in order to optimise the effectiveness of the initiator system used.

In the processes of the invention the acrylamidase enzyme may be applied to the polyacrylamide or acrylamide monomer in any suitable form. Normally it is applied in the form of a liquid suspension or solution. For instance it may be applied in the form of an aqueous solution of acrylamidase or as a reverse-phase emulsion of acrylamidase. It may be applied in the form of an aqueous suspension. In some processes the acrylamidase is applied in the pure (molecular) form, having been separated from the microorganism in which it was produced.

In other process it is present in the form of bacterial cells and/or cell debris, often as a paste, which contain an acrylamidase enzyme which can reduce acrylamide levels, for instance whole cell form. Cells and/or cell debris may be used in immobilised form, if appropriate, or preferably in free call form. Immobilisation may be in any suitable known manner, eg in a polyacrylamide matrix. Permeabilised cells or cell material can be used.

In a further aspect of the invention we provide a process of reducing the residual acrylamide content of a polyacrylamide, preferably a cationic or non-ionic polyacrylamide, by contacting it with cell material from Rhodococcus strain NCIMB 40889 or Rhodococcus strain NCIMB 40755 or a mutant of either having the ability to produce an acrylamidase. Preferably contact is made at an acidic pH, more preferably 2 to 5, particularly 3.0 to 4.5. The polyacrylamide may be in the form of for instance a gel, a liquid dispersion in non-aqueous liquid or an emulsion.

When any of the processes of the invention are used to treat polyacrylamides having residual acrylamide content, the residual acrylamide content before treatment may be for instance above 200 ppm, and often above 400 or 500 ppm. It may be above 1,000 ppm and even up to 2,000 ppm or more. In the invention it is possible to reduce the level of residual acrylamide to below 100 ppm, and even below 50 or 30 ppm, preferably below 20 or 10 ppm. It may also be possible to reduce levels to below those which are detectable. The level of acrylamide monomer after treatment is preferably not more than 50%, more preferably not more than 20% and in particular not more than 10%, of the level before treatment. It can even be bellow 5% or 1% of the level before treatment.

In this specification treatment of polyacrylamides and acrylamide monomer has been discussed. Any of the processes of the invention and uses of the acrylamidase enzymes of the invention are applicable equally to polymers of methacrylamide and reduction of residual methacrylamide monomer.

The invention will now be illustrated by reference to the following examples.

EXAMPLES

Examples 1 to 5 a) Gel Polymerisation

Gel polymerisations were carried out using 400 g monomer.

Monomer solutions (as detailed below) containing 100 ppm Tetralon B (sodium EDTA) were initiated from 0° C. after degassing with nitrogen.

The gels were cured for 4–5 hours at 80° C. before being minced. The wet gel was treated as required and then dried at 60° C.

b) Gel Treatment

Treatment of the wet gel with enzyme was carried out by contacting it with a suspension of cells containing amidase, in 0.9% saline solution or water.

The activity of the Amidase was taken to be 1250 units/g. The volume of Amidase (ie no. of units) to be added was calculated on the weight of the dry polymer present.

The treated gel was sealed in a plastic bag and left at room temperature for 30 minutes before being dried.

In these examples the amidase used was that obtained from the isolate NCIMB 40889.

After testing each dried sample was analysed for free acrylamide.

Example 1
Polymer A (homopolymer of acrylamide, IV 20 dl/g)
Effect of Adipic Acid Levels on Treatment Polyacrylamide gels with varying levels of Adipic acid were prepared at pH 4.

200 ppm AZDN (azodiiso butyronitrile) and 50 ppm VA044 (2,2'-azobis[2-(2-imidazolin-2-yl)propane] dihydrochloric acid) were used as thermal initiators with 12 ppm $KBrO_3$ and 6 ppm $Na_2SO_3$ as redox initiators.

75 g minced portions of wet gel were treated with the enzyme levels as indicated in Table 1 below.

Free ACM (acrylamide) results on the dried polymers are shown in Table 1.

TABLE 1

| Adipic Acid (%) | Amidase Units/g | Free ACM (ppm) |
|---|---|---|
| 0 | — | 433 |
| 0 | 10 | 203 |
| 0 | 40 | 44 |
| 1 | — | 592 |
| 1 | 10 | 348 |
| 1 | 40 | 159 |
| 2 | — | 885 |
| 2 | 10 | 215 |
| 2 | 40 | 154 |
| 5 | — | 636 |
| 5 | 10 | 506 |
| 5 | 40 | 224 |

Table 1 shows the decrease in free ACM level as the dose of amidase increases.

It can be seen from this table that as the adipic acid level present in the polymer increases then the effectiveness of the Amidase decreases.

However, it is noticeable and surprising that the relative activity of the microorganism and its acrylamidase enzyme remain relatively high even as the dose of adipic acid increases. In fact, the residual acrylamide level can be reduced by approximately 50% in the gel which contains 5% adipic acid. This is particularly surprising in view of the assay results given in the preferred tests for adipic acid tolerance described above. The microorganism and its acrylamidase enzyme appear to perform better in reducing residual acrylamide levels of a polymer gal than would be expected based on a simple assay.

Example 2
Polymer B (about 74 wt % acrylamide/about 22 wt % DMAEAqMeCl, IV 16.5 dl/g)
Effect of Adipic Acid Levels on Treatment
Polymer B gels with varying levels of Adipic Acid were prepared at pH 4.
100 ppm AZDN and 50 ppm VA044 were used as thermal initiators with 12 ppm $KBrO_3$ and 6 ppm $Na_2SO_3$ as redox initiators.
75 g minced portions of wet gel were treated with the enzyme levels as indicated in Table 2 below.
Free ACM results are also shown in Table 2.

TABLE 2

| Adipic Acid (%) | Amidase Units/g | Free ACM (ppm) |
|---|---|---|
| 0 | — | 1200 |
| 0 | 10 | 348 |
| 0 | 40 | 59 |
| 1 | — | 1400 |
| 1 | 10 | 666 |
| 1 | 40 | 255 |
| 2 | — | 1300 |
| 2 | 10 | 680 |
| 2 | 40 | 357 |
| 5 | — | 953 |
| 5 | 10 | 885 |
| 5 | 40 | 704 |

Table 2 shows the decrease in free ACM level as the Amidase dose increases.

It can be seen from this table that treating polymers containing up to 2% adipic acid reduces the residual ACM level in line with the dose level.

However at 5% adipic acid the residual ACM level only shows a small decrease in value.

Again however the effectiveness of the microorganism and its acrylamidase are surprisingly high. The amount of residual acrylamide is reduced significantly even at levels of 2% adipic acid.

Example 3
Effect of pH of Polymer B on Treatment
Polymer B gels with 5% Adipic Acid with varying pH were prepared.
100 ppm AZDN and 50 ppm VA044 were used as thermal initiators with 12 ppm $KBrO_3$ and 6 ppm Na2SO3 as redox initiators.
75 g minced portions of wet gel were treated with the enzyme levels as indicated in Table 3 below.
Free ACM results are also shown in Table 3.

TABLE 3

| pH | Amidase Units/g | Free ACM (ppm) |
|---|---|---|
| 3.5 | — | 1100 |
| 3.5 | 10 | 1100 |
| 3.5 | 40 | 473 |
| 4.0 | — | 953 |
| 4.0 | 10 | 865 |
| 4.0 | 40 | 704 |
| 4.5 | — | 2500 |
| 4.5 | 10 | 1400 |
| 4.5 | 40 | 1600 |

Table 3 shows the decrease in free ACM level as the Amidase dose level increases at different pH's.

Example 4
Further Treatments on Polymer B Gels
Polymer B gels with varying levels of adipic acid were prepared.
100 ppm AZDN and 50 ppm VA044 were used as thermal initiators with 12 ppm $KBrO_3$ and 6 ppm $Na_2SO_3$ as redox initiators.
75 g minced portions of wet gel were treated with the enzyme levels as indicated in Table 4 below.
Free ACM results are also shown in Table 4.

TABLE 4

| Adipic Acid (%) | Amidase Units/g | Free ACM (ppm) |
|---|---|---|
| 0 | — | 1100 |
| 0 | 40 | 131 |
| 1 | — | 1400 |
| 1 | 40 | 215 |
| 2 | — | 987 |
| 2 | 40 | 367 |
| 3 | — | 1400 |
| 3 | 40 | 655 |
| 4 | — | 1700 |
| 4 | 40 | 1100 |
| 5 | — | 1000 |
| 5 | 40 | 561 |

Table 4 shows the reduction in free ACM levels as the adipic acid level increases.

It can be seen that as the adipic acid level increase the Amidase enzyme reduces the free ACM level by a smaller amount.

Example 5
c) Polymer C (about 35 wt % acrylamide/about 61% DMAEAqMeCl, IV 13.5 dl/g)
Effect of AdiDic Acid Levels on Treatment
Polymer C gels with varying levels of Adipic Acid were prepared at pH 4.

200 ppm AZDN and 50 ppm VA044 were used as thermal initiators with 16 ppm KBrO$_3$ and 8 ppm Na$_2$SO$_3$ as redox initiators.

75 g minced portions of wet gel were treated with the enzyme levels as indicated in table 5 below.

Free ACM results are also shown in Table 5.

TABLE 5

| Adipic Acid (%) | Amidase Units/g | Free ACM (ppm) |
|---|---|---|
| 0 | — | 332 |
| 0 | 40 | 185 |
| 1 | — | 1300 |
| 1 | 40 | 538 |
| 2 | — | 452 |
| 2 | 40 | 194 |
| 3 | — | 406 |
| 3 | 40 | 143 |
| 4 | — | 314 |
| 4 | 40 | 112 |
| 5 | — | 240 |
| 5 | 40 | 213 |

Table 5 shows the reduction in free ACM levels as the adipic acid level increases.

It can be seen from this table that a Polymer C gel containing up to 4% adipic acid when treated with Amidase shows a reduction in free ACM level.

Again it can be seen that even in a gel containing 4% adipic acid the microorganism and its acrylamidase can reduce residual acrylamide by approximately 60%. This also is surprising in view of the assay results described above.

EXAMPLE 6

Polymer gel samples were produced and treated with acrylamidase enzyme as in Examples 1 to 5. Details of the acrylamidase are given below.

Evaluation of NCIMB 40889

Sets of polyACM gels with and without Adipic Acid were pH 4.

200 ppm AZDN and 25 ppm VA044 were used as thermal initiators with 12 ppm KBrO$_3$ and 6 ppm Na$_2$SO$_3$ as redox initiators.

75 g minced portions of wet gel were treated with the as indicated in Table 6 below.

TABLE 6

| Adipic Acid (%) | Amidase (Units/g) | Free ACM (ppm) |
|---|---|---|
| 0 | — | 2300 |
| 0 | 11.6 | 124 |
| 0 | 11.6 | 134 |
| 1 | — | 1600 |
| 1 | 205 | 184 |
| 1 | 205 | 260 |

These results show the enzyme will reduce free ACM in polyACM gels when adipic acid is present.

Example 7

Evaluation of NCIMB 40889 (second culture)

Further polyACM gels with varying levels of Adipic prepared with the monomer pH at 4.0.

Initiator levels were as those in the previous section.

75 g minced portions of wet gel were treated with the enzyme levels indicated in Table 7 below.

Free ACM results are shown in Table 7.

TABLE 7

| Adipic Acid (%) | Amidase (Units/g) | Free ACM (ppm) |
|---|---|---|
| 0 | 0 | 2200 |
| 0 | 10 | 287 |
| 0 | 40 | 99 |
| 0 | 200 | 47 |
| 1 | 0 | 1700 |
| 1 | 10 | 616 |
| 1 | 40 | 206 |
| 1 | 200 | 62 |
| 2 | 0 | 2100 |
| 2 | 10 | 2000 |
| 2 | 40 | 685 |
| 2 | 200 | 126 |

From the results it can be seen that increasing the level of Amidase enzyme resulted in a greater reduction in residual ACM levels.

Increasing the adipic acid level resulted in the Amidase enzyme activity being reduced ie as adipic acid level increases a larger dose of Amidase is required to give equivalent residual ACM reduction.

However, the enzyme did show activity even in the presence of 2% adipic acid which enabled it to reduce free acrylamide from 2100 ppm to only 126 ppm. Although a larger amount of amidase is required, the microorganism used has a very high specific amidase activity and thus the quantities of bacterial cells required are not very high. The Table also shows that this microorganism can, in the absence of adipic acid but at pH 4, reduce free acrylamide levels to below 100 ppm under the tested conditions.

Example 8

This example demonstrates the effectiveness of the acrylamidase produced by the microorganism NCIMB 40755 at reducing acrylamide levels at low pH.

a) Gel Polymerisation

Standard gel polymerisation were carried out as in Examples 1 to 5 above.

Unless otherwise stated the gels did not contain adipic acid. Thermal initiator levels were generally low to provide gels with "high" free ACM levels.

Monomer solutions (as detailed in the text) containing 100 ppm Tetralon B were initiated from 0° C. after degassing with nitrogen.

The gels were cured for 4–5 hours at 80° C. before being minced. The wet gel was treated as required and then dried at 60° C.

b) Gel Polymer Processing—Amidase Treatment

Treatment of the wet gel with enzyme was carried out as in Examples 1 to 5 above. The volume of Amidase (ie no. of units) to be added was calculated on the weight of polymer present.

The Amidase sample was diluted with 0.9% saline solution to give an activity of 48 units/ml.

Fresh solution was prepared for each treatment. The treated gel was sealed in a plastic bag and left at room temperature for the required period of time before being dried.

The amidase used was that produced by the microorganism NCIMB 40755.

After treatment each dried sample was analysed for free acrylamide levels.

Effect of pH on Amidase Treatment

Polyacrylamide gel polymers were produced at pH 4, 5 and 6. The gels did not contain either Adipic Acid or Urea.

The gels prepared at pH 4 contained 25 ppm VA044 as a thermal initiator with varying levels of $KBrO_3$ and $Na_2SO3$ as redox initiators.

Those gels prepared at pH 5 and 6 used the t-BHP/$Na_2SO_3$ initiation system. All gels prepared contained 200 ppm AZDN as thermal initiator.

100 g minced portions of wet gel were treated with 10 and 25 units/g dry polymer Amidase and left for 30 minutes at room temperature before drying.

Free ACM results are shown in Table a below.

TABLE 8

| pH of gel | Amidase units/g dry polymer | Free ACM (ppm) |
|---|---|---|
| 4 | — | 1000 |
| 4 | 10 | 260 |
| 4 | 25 | 121 |
| 4 | — | 1100 |
| 4 | 10 | 103 |
| 4 | 25 | 116 |
| 5 | — | 10100 |
| 5 | 10 | 118 |
| 5 | 25 | 95 |
| 6 | — | 3200 |
| 6 | 10 | 215 |
| 6 | 25 | 147 |

It can be seen from the results that regardless of the pll of the gel and the initial residual ACM level the sample of Amidase was able to reduce all free ACM levels to below 300 ppm.

Effect of Adipic Acid on Amidase Treatment i) @ pH 4

A set of gels with varying levels of Adipic Acid was prepared at pH 4.

200 ppm AZDN was used as a thermal initiator with 7 ppm $KBrO_3$ and 14 ppm $Na_2SO_3$ as redox initiators.

100 g ACM results are shown in Table 9 below.

TABLE 9

| Adipic Acid (%) | Amidase Units/g | Free ACM (ppm) |
|---|---|---|
| 0 | — | 919 |
| 0 | 10 | 260 |
| 1 | — | 982 |
| 1 | 10 | 704 |
| 2 | — | 1100 |
| 2 | 10 | 657 |
| 5 | — | 1100 |
| 5 | 10 | 830 |

From the results it can be seen that for the gels containing Adipic Acid at pH 4 the residual ACM level was not significantly reduced when treated with Amidase enzyme. The gel sample without Adipic Acid gave a reduction in line with what would be expected.

ii) @ pH 6

Several gels with varying amounts of Adipic Acid were prepared at pH 6, ie the adipic acid will be present mainly as sodium adipate. 200 ppm AZDN was used at thermal initiator with 7 ppm t-BHP and 14 ppm $Na_2SO_3$ as redox initiators.

100 g minced portions of wet gel were treated with 10 units/g Amidase and left for 30 minutes at room temperature before drying.

Free ACM results are shown in Table 10 below.

TABLE 10

| Adipic Acid (%) | Amidase (Units/g) | Free ACM (ppm) |
|---|---|---|
| 0 | — | 4700 |
| 0 | 10 | 2400 |
| 1 | — | 5400 |
| 1 | 10 | 271 |
| 2 | — | 3400 |
| 2 | 10 | 366 |
| 5 | — | 3200 |
| 5 | 10 | 196 |

From the results shown it can be seen that all samples treated with Amidase showed a reduction in residual ACM level.

These results demonstrate that this microorganism and its acrylamidase are effective at reducing free acrylamide at both pH 6 and pH 4, but tend to be less effective in the presence of adipic acid at pH 4. At pH 6 the adipic acid is less inhibitory. This may indicate that it is the acid form which is inhibitory and that the adipate form, which is present at pH 6, is not problematic.

We claim:

1. An acrylamidase enzyme which has an acrylamidase activity at pH 4.0 in the presence of 15 mM adipic acid which is at least 30% of its acrylamidase activity measured at pH 4.0 in the absence of adipic acid.

2. An acrylamidase enzyme which can be produced by culturing Rhodococcus strain NCIMB 40889.

3. An acrylamidase enzyme which can be produced by culturing Rhodococcus strain NCIMB 40755.

4. Rhodococcus strain NCIMB 40889.

5. Rhodococcus strain NCIMB 40755.

* * * * *